United States Patent [19]

Bastian

[11] 4,183,943

[45] Jan. 15, 1980

[54] ORGANIC COMPOUNDS

[75] Inventor: Jean-Michel Bastian, Therwil, Switzerland

[73] Assignee: Sandoz Ltd., Basel, Switzerland

[21] Appl. No.: 875,114

[22] Filed: Feb. 3, 1978

[30] Foreign Application Priority Data

Feb. 8, 1977 [CH] Switzerland ........................ 1489/77
Mar. 18, 1977 [CH] Switzerland ........................ 3423/77
Mar. 18, 1977 [CH] Switzerland ........................ 3424/77

[51] Int. Cl.$^2$ ...................... A01N 9/00; C07D 333/24
[52] U.S. Cl. ...................................... 424/275; 549/43; 549/48
[58] Field of Search ................ 260/332.2 A, 332.2 R, 260/332.2 C; 424/275

[56] References Cited

U.S. PATENT DOCUMENTS 3,953,468  4/1976  Wechter et al. ............... 260/332.2 R
4,052,412  10/1977  Bastian ........................... 260/332.2 A Primary Examiner—Alan Siegel Attorney, Agent, or Firm—Gerald D. Sharkin; Robert S. Honor; Thomas O. McGovern

[57] ABSTRACT

The present invention provides compounds of formula,

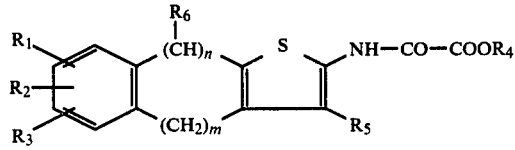

wherein n is from 0 to 4, m is from 0 to 4, whereby n+m is at least 1 and not more than 4, each of $R_1$, $R_2$, $R_3$ and $R_4$ may independently be, for example, hydrogen, alkyl or alkoxy, $R_5$ may, for example, be nitrile or carbamoyl and $R_6$ is hydrogen and, when n is 2 and m is 0, one of $R_6$ can be alkyl of 1 to 4 carbon atoms, which compounds possess pharmaceutical, for example antiallergic, activity.

32 Claims, No Drawings

ORGANIC COMPOUNDS

The present invention relates to 8H-indeno[2,1-b]thiophen-2-oxaminic acids and esters thereof.

More particularly, the present invention provides compounds of formula I,

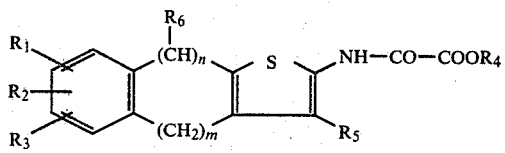
I wherein
n is from 0 to 4,
m is from 0 to 4,
whereby n+m is at least 1 and not greater than 4,
$R_1$ is hydrogen, halogen of atomic number from 9 to 35, alkyl of 1 to 4 carbon atoms or alkoxy of 1 to 4 carbon atoms,
$R_2$ is hydrogen, alkyl of 1 to 4 carbon atoms or alkoxy of 1 to 4 carbon atoms,
$R_3$ is hydrogen, alkyl of 1 to 4 carbon atoms or alkoxy of 1 to 4 carbon atoms,
whereby not more than one of the substituents $R_1$, $R_2$ and $R_3$ can be branched alkyl or alkoxy,
$R_4$ is hydrogen or alkyl of 1 to 4 carbon atoms,
$R_5$ is nitrile, carbamoyl or carboxyl when $R_4$ is hydrogen, and
$R_5$ is nitrile carbamoyl or $COOR_7$, wherein $R_7$ is alkyl of 1 to 4 carbon atoms, when $R_4$ is alkyl of 1 to 4 carbon atoms, and
$R_6$ is hydrogen or, when n is 2 and m is 0, one of $R_6$ can be alkyl of 1 to 4 carbon atoms.

n is preferably 1, 2 or 3, especially 1. n can also be 0 or 4.

m is preferably 0. m can also be 1, 2, 3 or 4. Especially preferred compounds are those wherein n is 1 and m is 0.

$R_1$ can be hydrogen. When $R_1$ is halogen of atomic number from 9 to 35, this is preferably chlorine. When $R_1$ is alkyl or alkoxy, these preferably contain 1 or 2 carbon atoms and are especially methyl or methoxy.

$R_2$ can be hydrogen. When $R_2$ is alkyl or alkoxy, these preferably contain 1 or 2 carbon atoms and are especially methyl or methoxy.

$R_3$ can be hydrogen. When $R_3$ is alkyl or alkoxy, these preferably contain 1 or 2 carbon atoms and are especially methyl or methoxy.

$R_1$, $R_2$ and $R_3$ especially signify hydrogen or methoxy.

$R_4$ can be hydrogen. When $R_4$ is alkyl, this may, for example, be ethyl or methyl.

$R_5$ can be nitrile. $R_5$ can also be carbamoyl. When $R_4$ is hydrogen, $R_5$ can be carboxy. When $R_4$ is alkyl of 1 to 4 carbon atoms, $R_5$ can be $COOR_7$ wherein $R_7$ is alkyl of 1 to 4 carbon atoms. $R_5$ is preferably nitrile or carbamoyl.

$R_6$ can be hydrogen. When $R_6$ is alkyl, this is preferably methyl.

The invention further provides a process for the production of a compound of formula I comprising,
(a) producing a compound of formula Ia,

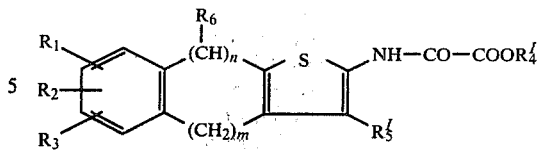
Ia wherein
n, m, $R_1$, $R_2$, $R_3$ and $R_6$ are as previously defined,
$R_4^I$ is alkyl of 1 to 4 carbon atoms, and
$R_5^I$ is nitrile, carbamoyl or $COOR_7$ as previously defined,
by introducing the group $-CO-COOR_4^I$, wherein $R_4^I$ is as previously defined, into a compound of formula II,

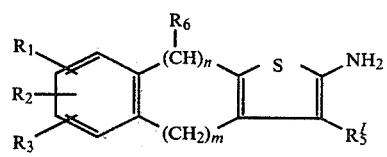
II wherein n, m, $R_1$, $R_2$, $R_3$, $R_5^I$ and $R_6$ are as previously defined, or
(b) producing a compound of formula Ib,

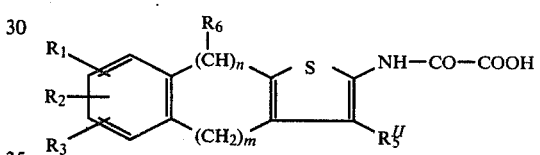
Ib wherein
n, m, $R_1$, $R_2$, $R_3$ and $R_6$ are as previously defined, and
$R_5^{II}$ is nitrile, carbamoyl or carboxyl,
by hydrolysing a compound of formula Ia as previously defined.

Process variant (a) can be effected according to known methods for the acylation of amines. The usual acylating materials may be employed, such as the chloride or bromide of an acid of formula III,

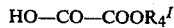
HO—CO—COOR$_4^I$     III wherein $R_4^I$ is as defined above.

The reaction can be effected in the presence of an inert organic solvent, conveniently in the presence of an acid binding agent. The reaction temperature is preferably between 0° C. and the boiling point of the reaction mixture, especially between 0° C. and room temperature.

Process variant (b) can be effected according to known methods for the removal of ester groups. When $R_5^I$ is $COOR_7$, this is simultaneously hydrolysed to carboxy. When $R_5^I$ is nitrile or carbamoyl, the process is effected under mild conditions to avoid attack of the $R_5^I$ group. The hydrolysis may, for example, be effected in the presence of an equivalent quantity of a base, for example, an alkalimetal or an alkaline earth metal hydroxide. The reaction may be effected at a temperature between ca. 0° C. and the boiling point of the reaction mixture, preferably at room temperature, and, if desired, with the addition of an inert organic solvent which is miscible with water.

The resulting compounds of formula I may be isolated and purified using conventional techniques.

The compounds of formula I may be converted into salt forms and vice versa. When $R_5$ is carboxyl and/or $R_4$ is hydrogen, salt forms may be prepared by reacting the compound of formula I with strong bases such as alkali metal hydroxides or with organic bases such as triethylamine and cyclohexylamine.

The starting materials of formula II are either known or may be obtained in known manner by condensing a compound of formula IV,

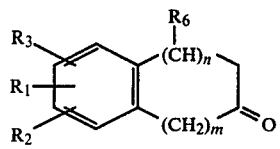

IV wherein n, m, $R_1$, $R_2$, $R_3$ and $R_6$ are as previously defined,
with a compound of formula V,

V wherein $R_5^I$ is as previously defined,
and reacting the product so obtained with sulphur.

Insofar as the production of the starting materials has not been described herein, these compounds are either known or can be produced by known methods or by methods analogous to those described herein or by methods analogous to known methods.

In the following Examples, all temperatures are in degrees Celsius.

EXAMPLE 1:
3-Cyano-8H-indeno[2,1-b]thiophen-2-oxaminic acid methyl ester

[Process variant (a)]

A solution of 6.4 g of methyl oxalate chloride in 40 ml of anhydrous methylene chloride is added dropwise at a temperature of 5° to a solution of 2-amino-8H-indeno[2,1-b]thiophen-3-carboxy nitrile and 7.6 g of pyridine in 150 ml of anhydrous methylene chloride. The reaction mixture is stirred for 7 hours at room temperature, diluted with methylene chloride and poured onto water. The organic solution is separated, the aqueous phase further extracted with methylene chloride and the combined organic solutions washed neutral with water. After drying over magnesium sulphate, the solvent is evaporated off and the title compound, which remains as a crystalline residue, is washed with ether. M.P. 223°–225°.

The following compounds can be prepared in manner analogous to that described in Example 1, using appropriate starting materials in approximately equivalent amounts.

| Ex. No. | n | m | $R_1$ | $R_2$ | $R_3$ | $R_4^I$ | $R_5^I$ | $R_6$ | M.P. |
|---|---|---|---|---|---|---|---|---|---|
| 2 | 2 | 0 | H | H | H | —CH$_3$ | —CN | H | 191°–192° |
| 3 | 2 | 0 | 7-OCH$_3$ | H | H | " | " | H | 241°–243° |
| 4 | 2 | 0 | 6-OCH$_3$ | 7-OCH$_3$ | 8-OCH$_3$ | " | " | H | 201°–202° |
| 5 | 1 | 0 | H | H | H | " | —CONH$_2$ | H | 269°–270° |
| 6 | 0 | 1 | H | H | H | " | —CN | H | 245°–247° |
| 7 | 0 | 2 | 7-OCH$_3$ | H | H | " | " | H | 230°–232° |
| 8 | 0 | 2 | H | H | H | " | " | H | 208°–210° |
| 9 | 0 | 3 | H | H | H | " | " | H | 160°–162° |
| 10 | 2 | 0 | H | H | H | " | " | H | 159°–160° |
| 11 | 1 | 2 | H | H | H | " | " | H | 189°–191° |
| 12 | 1 | 2 | H | H | H | —C$_2$H$_5$ | —CONH$_2$ | H | 225°–227° |
| 13 | 2 | 0 | H | H | H | —CH$_3$ | —CN | 5-CH$_3$ | 213°–214° |

EXAMPLE 14:
3-Cyano-8H-indeno[2,1-b]thiophen-2-oxaminic acid

[Process variant (b)]

A solution of 3.5 g of potassium hydroxide in 70 ml of water is added to a solution of 7.0 g of 3-cyano-8H-indeno[2,1-b]thiophen-2-oxaminic acid methyl ester in 140 ml of dioxan and stirred at room temperature for one hour. The reaction mixture is acidified, under cooling, with 2 N hydrochloric acid (to pH 1). The title compound, which precipitates, is filtered off and throughly washed, first with water and then with acetone and ether. M.P. 270° (Decomp.).

The following compounds can be prepared in manner analogous to that of Example 14, using appropriate starting materials in approximately equivalent amounts.

| Ex. No. | n | m | $R_1$ | $R_2$ | $R_3$ | $R_5^{II}$ | $R_6$ | M.P. |
|---|---|---|---|---|---|---|---|---|
| 15 | 2 | 0 | H | H | H | —CN | H | 225°–227° |
| 16 | 2 | 0 | 7-OCH$_3$ | H | H | " | H | 299°–301° |
| 17 | 2 | 0 | 6-OCH$_3$ | 7-OCH$_3$ | 8-OCH$_3$ | " | H | 204°–205° |
| 18 | 1 | 0 | H | H | H | —CONH$_2$ | H | Decomp. over 300° |
| 19 | 2 | 0 | H | H | H | " | H | 241°–243° |
| 20 | 0 | 1 | H | H | H | —CN | H | Decomp. 255° |
| 21 | 0 | 2 | 7-OCH$_3$ | H | H | " | H | 299°–301° |
| 22 | 0 | 2 | H | H | H | " | H | 225°–227° |
| 23 | 0 | 3 | H | H | H | " | H | 254°–255° |
| 24 | 2 | 0 | 7-OCH$_3$ | 8-OCH$_3$ | H | " | H | 234°–235° |

-continued

| Ex. No. | n | m | $R_1$ | $R_2$ | $R_3$ | $R_5$ | $R_6$ | M.P. |
| --- | --- | --- | --- | --- | --- | --- | --- | --- |
| 25 | 3 | 0 | H | H | H | " | H | 241°–242° |
| 26 | 1 | 2 | H | H | H | " | H | 216°–217° |
| 27 | 1 | 2 | H | H | H | —CONH$_2$ | H | Decomp. 230° |
| 28 | 2 | 0 | H | H | H | —CN | 5-CH$_3$ | 217°–218° |
| 29 | 1 | 2 | H | H | H | —COOH | H | 225°–227° |

The compounds of formula I possess pharmacological activity. In particular, the compounds possess disodium chromoglycate (DSCG)-like activity, and are therefore useful in the treatment and prophylaxis of allergic conditions, such as allergic asthma, exercise-induced asthma and allergic gastro-intestinal disorders, as indicated in the passive cutaneous anaphylaxis (PCA) test in the rat.

The method employed is based on those described by Mota [1], Stotland and Share [2] and Perper et al. [3]. Female rats (180–200 g) are sensitized by subcutaneous administration of 1 mg of ovalbumin (Fluka No. 05430) and 200 mg of aluminium hydroxide gel (Merck No. 1088), dissolved in 1 ml of 0.9% saline, and intraperitoneal administration of 0.5 ml of Haemophilus pertussis vaccine (Schweizerisches Serum- und Impfinstitut, Bern, No. 115,325; 4×10$^{10}$ organism/ml). Fourteen days later, the animals are exsanguinated, the blood centrifuged and the serum (anti-ovalbumin serum) collected and deep frozen.

[1] Mota, I., Immunology 7, 681 (1964).
[2] Stotland, M. and Share, N. N., Can. J. Physiol. Pharmacol. 52, 1114 (1974).
[3] Perper, R. J., Oronsky, A. L. and Blancuzzi, V., J. Allergy Clin. Immunol. 53, 66 (1974).

The anti-ovalbumin serum is injected intradermally (0.1 ml of a 1:100 to 1:200 dilution per injection site) at three sites on the backs of untreated, female rats. Twenty-four hours later (intravenous testing) or forty-eight hours later (oral testing), the rats receive either solvent or the test compound (2 ml/kg i.v. 0.1 to 3.2 mg/kg i.v. or 5 ml/kg p.o. 1 to 32 mg/kg p.o.) followed one minute (intravenous testing), or 7.5 or 15 minutes (oral testing) later by the intradermal injection of histamine (8 μg in 0.05 ml of 0.9% saline) and serotonin (0.5 μg in 0.05 ml of 0.9% saline) at two further sites. Immediately afterwards, the animals receive an intravenous injection of 1 ml of a 0.9% saline solution containing 5 mg of ovalbumin (twice crystallised) and 2.5 mg of Evans blue dye. The ovalbumin, histamine and serotonin elicit a cutaneous anaphylactic/anaphylactoid reaction, the intensity of which is proportional to the distance to which the dye diffuses into the tissue surrounding the seven sensitisation sites. Thirty minutes later, the rats are killed by CO$_2$ inhalation and the diameter in mm of the blue spot at each anti-ovalbumin serum, histamine and serotonin injection site measured. The drug dose decreasing the diameter of the blue area by 50% compared with solvent pretreated control rats (ED50), is obtained from the regression line. The dose-effect correlation is tested for statistical significance.

The DSCG-like activity, in particular histamine release inhibitor activity, can be confirmed by inhibition of histamine release in the passive peritoneal anaphylaxis test in the rat.

Rats are passively sensitised by intraperitoneal injection of 3 ml of 1:2 to 1:10 diluted rat anti-ovalbumin serum. Twenty-four hours later, the rats are treated intravenously (0.1 to 3.2 mg/kg i.v.) with the test compound. Immediately after intravenous application, the anaphylactic reaction is elicited by intravenous administration of 1 ml of 0.5% ovalbumin, immediately followed by 5 ml of HBSS (Hank's balanced salt solution) intraperitoneally. Five minutes later, the animals are decapitated and the peritoneal fluid collected and kept in an ice bath. After centrifugation for 5 minutes (350 g) at 4° C., the histamine content of the supernatant liquid is estimated fluorophotometrically [4]. The effects of the test compounds are expressed as percentage changes in histamine release compared with controls.

[4] Kusner, E. J. and Herzig, D. J., In: Advances in Automated Analysis, vol. II, Thurman Associates, Miami (1971).

The compounds may be administered in free form or in pharmaceutically acceptable salt form. Such salts possess the same order of activity as the free form and are readily prepared in conventional manner. Examples of suitable bases include alkali metal hydroxides, triethylamine and cyclohexylamine.

The invention also provides a pharmaceutical composition comprising a compound of formula I, in free form or in pharmaceutically acceptable salt form in association with a pharmaceutically acceptable diluent or carrier. Such compositions may be in the form of, for example, a capsule, solution or spray.

In one group of compounds, $R_1$, $R_2$, $R_3$, $R_4$ and $R_5$ are as previously defined, $R_6$ is hydrogen, n is 1 to 4 and m is 0.

In a second group of compounds, $R_1$, $R_2$, $R_3$, $R_4$ and $R_5$ are as previously defined, m is 1 to 4 and n is 0.

In a third group of compounds, $R_4$ is as previously defined, $R_1$ is as previously defined and is in position 7- or 8-, each of $R_2$ and $R_3$ is hydrogen, $R_5$ is nitrile or carbamoyl, $R_6$ is hydrogen, m is 2 and n is 1.

What is claimed is:

1. A compound of formula,

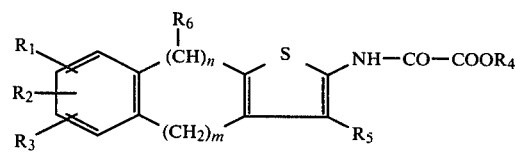

wherein
n is from 0 to 4,
m is from 0 to 4,
whereby n+m is at least 1 and not greater than 4,
$R_1$ is hydrogen, halogen of atomic number from 9 to 35, alkyl of 1 to 4 carbon atoms or alkoxy of 1 to 4 carbon atoms,
$R_2$ is hydrogen, alkyl of 1 to 4 carbon atoms or alkoxy of 1 to 4 carbon atoms,
$R_3$ is hydrogen, alkyl of 1 to 4 carbon atoms or alkoxy of 1 to 4 carbon atoms,
whereby not more than one of the substituents $R_1$, $R_2$ and $R_3$ can be branched alkyl or alkoxy,
$R_4$ is hydrogen or alkyl of 1 to 4 carbon atoms,
$R_5$ is nitrile, carbamoyl or carboxyl when $R_4$ is hydrogen, and $R_5$ is nitrile carbamoyl or $COOR_7$, wherein $R_7$ is alkyl of 1 to 4 carbon atoms, when $R_4$ is alkyl of 1 to 4 carbon atoms, and $R_6$ is hydrogen or, when n is 2 and m is 0, one of $R_6$ can be alkyl of 1 to 4 carbon atoms, in free form or in the form of a pharmaceutically acceptable salt.

2. A compound of claim 1, wherein each of $R_2$, $R_3$, $R_4$ and $R_6$ is hydrogen, $R_1$ is 7-$OCH_3$, $R_5$ is CN, n is 2 and m is 0.

3. A pharmaceutical composition comprising a therapeutically effective amount of a compound of claim 1 in association with a pharmaceutically acceptable diluent or carrier.

4. A method of preventing or treating allergic conditions which comprises administering to an animal in need of such treatment an effective amount of a compound of claim 1.

5. The compound of claim 1 which is 3-cyano-8H-indeno[2,1-b]thiophen-2-oxaminic acid methyl ester.

6. The compound of claim 1 in which n, m, $R_1$, $R_2$, $R_3$, $R_4$, $R_5$ and $R_6$ are 2, 0, H, H, H, —$CH_3$, —CN and H, respectively.

7. The compound of claim 1 in which n, m, $R_1$, $R_2$, $R_3$, $R_4$, $R_5$ and $R_6$ are 2, 0, 7-$OCH_3$, H, H, —$CH_3$, —CN and H, respectively.

8. The compound of claim 1 in which n, m, $R_1$, $R_2$, $R_3$, $R_4$, $R_5$ and $R_6$ are 2, 0, 6-$OCH_3$, 7-$OCH_3$, 8-$OCH_3$, —$CH_3$, —CN and H, respectively.

9. The compound of claim 1 in which n, m, $R_1$, $R_2$, $R_3$, $R_4$, $R_5$ and $R_6$ are 1, 0, H, H, H, —$CH_3$, —$CONH_2$ and H, respectively.

10. The compound of claim 1 in which n, m, $R_1$, $R_2$, $R_3$, $R_4$, $R_5$ and $R_6$ are 0, 1, H, H, H, —$CH_3$, —CN and H, respectively.

11. The compound of claim 1 in which n, m, $R_1$, $R_2$, $R_3$, $R_4$, $R_5$ and $R_6$ are 0, 2, 7-$OCH_3$, H, H, —$CH_3$, —CN and H, respectively.

12. The compound of claim 1 in which n, m, $R_1$, $R_2$, $R_3$, $R_4$, $R_5$ and $R_6$ are 0, 2, H, H, H, —$CH_3$, —CN and H, respectively.

13. The compound of claim 1 in which n, m, $R_1$, $R_2$, $R_3$, $R_4$, $R_5$ and $R_6$ are 0, 3, H, H, H, —$CH_3$, —CN and H, respectively.

14. The compound of claim 1 in which n, m, $R_1$, $R_2$, $R_3$, $R_4$, $R_5$ and $R_6$ are 1, 2, H, H, H, —$CH_3$, —CN and H, respectively.

15. The compound of claim 1 in which n, m, $R_1$, $R_2$, $R_3$, $R_4$, $R_5$ and $R_6$ are 1, 2, H, H, H, —$C_2H_5$, —$CONH_2$ and H, respectively.

16. The compound of claim 1 in which n, m, $R_1$, $R_2$, $R_3$, $R_4$, $R_5$ and $R_6$ are 2, 0, H, H, H, —$CH_3$, —CN and 5-$CH_3$, respectively.

17. The compound of claim 1 which is 3-cyano-8H-indeno[2,1-b]thiophen-2-oxaminic acid.

18. The compound of claim 1 in which $R_4$ is hydrogen and n, m, $R_1$, $R_2$, $R_3$, $R_5$ and $R_6$ are 2, 0, H, H, H, —CN and H, respectively.

19. The compound of claim 1 in which $R_4$ is hydrogen and n, m, $R_1$, $R_2$, $R_3$, $R_5$ and $R_6$ are 2, 0, 7-$OCH_3$, H, H, —CN and H, respectively.

20. The compound of claim 1 in which $R_4$ is hydrogen and n, m, $R_1$, $R_2$, $R_3$, $R_5$ and $R_6$ are 2, 0, 6-$OCH_3$, 7-$OCH_3$, 8-$OCH_3$, —CN and H, respectively.

21. The compound of claim 1 in which $R_4$ is hydrogen and n, m, $R_1$, $R_2$, $R_3$, $R_5$ and $R_6$ are 1, 0, H, H, H, —$CONH_2$ and H, respectively.

22. The compound of claim 1 in which $R_4$ is hydrogen and n, m, $R_1$, $R_2$, $R_3$, $R_5$ and $R_6$ are 2, 0, H, H, H, —$CONH_2$ and H, respectively.

23. The compound of claim 1 in which $R_4$ is hydrogen and n, m, $R_1$, $R_2$, $R_3$, $R_5$ and $R_6$ are 0, 1, H, H, H, —CN and H, respectively.

24. The compound of claim 1 in which $R_4$ is hydrogen and n, m, $R_1$, $R_2$, $R_3$, $R_5$ and $R_6$ are 0, 2, 7-$OCH_3$, H, H, —CN and H, respectively.

25. The compound of claim 1 in which $R_4$ is hydrogen and n, m, $R_1$, $R_2$, $R_3$, $R_5$ and $R_6$ are 0, 2, H, H, H, —CN and H, respectively.

26. The compound of claim 1 in which $R_4$ is hydrogen and n, m, $R_1$, $R_2$, $R_3$, $R_5$ and $R_6$ are 0, 3, H, H, H, —CN and H, respectively.

27. The compound of claim 1 in which $R_4$ is hydrogen and n, m, $R_1$, $R_2$, $R_3$, $R_5$ and $R_6$ are 2, 0, 7-$OCH_3$, 8-$OCH_3$, H, —CN and H, respectively.

28. The compound of claim 1 in which $R_4$ is hydrogen and n, m, $R_1$, $R_2$, $R_3$, $R_5$ and $R_6$ are 3, 0, H, H, H, —CN and H, respectively.

29. The compound of claim 1 in which $R_4$ is hydrogen and n, m, $R_1$, $R_2$, $R_3$, $R_5$ and $R_6$ are 1, 2, H, H, H, —CN and H, respectively.

30. The compound of claim 1 in which $R_4$ is hydrogen and n, m, $R_1$, $R_2$, $R_3$, $R_5$ and $R_6$ are 1, 2, H, H, H, —$CONH_2$ and H, respectively.

31. The compound of claim 1 in which $R_4$ is hydrogen and n, m, $R_1$, $R_2$, $R_3$, $R_5$ and $R_6$ are 2, 0, H, H, H, —CN and 5-$CH_3$, respectively.

32. The compound of claim 1 in which $R_4$ is hydrogen and n, m, $R_1$, $R_2$, $R_3$, $R_5$ and $R_6$ are 1, 2, H, H, H, —COOH and H, respectively.

* * * * *